United States Patent [19]

Collins et al.

[11] Patent Number: 4,589,277
[45] Date of Patent: May 20, 1986

[54] PROCESS AND APPARATUS FOR DETERMINING THE PERCENTAGE OF A LIQUID CONTAINED IN A LIQUID MIXTURE

[76] Inventors: Hans-Jürgen Collins, Im Sieke 45; Kurt Lhotzky, Heimgarten 17a, both of 3300 Braunschweig, Fed. Rep. of Germany

[21] Appl. No.: 629,839
[22] PCT Filed: Nov. 11, 1983
[86] PCT No.: PCT/EP83/00297
 § 371 Date: Jun. 29, 1984
 § 102(e) Date: Jun. 29, 1984
[87] PCT Pub. No.: WO84/02003
 PCT Pub. Date: May 24, 1984

[30] Foreign Application Priority Data

Nov. 18, 1982 [DE] Fed. Rep. of Germany ....... 3242506

[51] Int. Cl.⁴ .................. G01K 7/16; G01N 27/18
[52] U.S. Cl. .................. 73/61.1 R; 73/61.3; 374/54
[58] Field of Search ........... 73/61.3, 61.1 R; 374/16, 27, 43, 44, 45, 54

[56] References Cited

U.S. PATENT DOCUMENTS

| | | | |
|---|---|---|---|
| 1,836,316 | 12/1931 | Esau | 374/45 |
| 2,779,189 | 1/1957 | Corneil | 374/54 X |
| 4,106,331 | 8/1978 | Bunton et al. | 73/61.3 X |
| 4,220,041 | 9/1980 | Potter | 73/61.1 R |
| 4,408,902 | 10/1983 | Peuker | 73/61.3 X |
| 4,501,145 | 2/1985 | Boegli et al. | 374/44 X |

FOREIGN PATENT DOCUMENTS 0056424 1/1981 European Pat. Off. .
2721732 11/1978 Fed. Rep. of Germany .

Primary Examiner—Stewart J. Levy
Assistant Examiner—Joseph W. Roskos
Attorney, Agent, or Firm—Karl F. Ross; Herbert Dubno

[57] ABSTRACT

During a process for determining the percentage of a given liquid contained in a liquid mixture, the given liquid having a lower evaporation temperature than the rest of the mixture, an observed spontaneous change in an electric resistance wire, which is immersible into the liquid mixture, while temporarily applying a predetermined energy quantity and thus heating the wire until the liquid mixture reaches or exceeds boiling temperature, is used for determining suitable measured quantities. When supplying a specific and defined energy quantity, having been determined in a representative sample, for heating the wire to the boiling point of the liquid mixture, either the energy conversion, which occurred during this time interval with a constant time interval for the energy supply, or the time interval for the energy conversion, which occurred with a given energy quantity, is measured and compared with the corresponding measured quantities determined in the sample.

12 Claims, 3 Drawing Figures

PROCESS AND APPARATUS FOR DETERMINING THE PERCENTAGE OF A LIQUID CONTAINED IN A LIQUID MIXTURE

FIELD OF THE INVENTION

This invention relates to a process for determining when a given percentage acting as a limiting value of a portion of a particular liquid contained in a liquid mixture is reached or exceeded, the portion having a lower evaporation temperature than the rest of the liquid, particularly for determining the water contained in a brake fluid, as well as a device for executing the process.

BACKGROUND OF THE INVENTION

Aforesaid processes and devices, particularly for determining the percentage limiting value of a brake fluid, are known which are based on the established fact that by increasing the water content in the brake fluid the boiling point of this fluid or liquid mixture is reduced, and thus represents a measurement for the portion of the water contained in the brake fluid.

With the known processes, a sample is always taken from the liquid and heated in a test chamber, until vaporization takes place in connection with a temperature measurement and an admission check of the test chamber, so as to obtain the temperature measurement as a measurement for the boiling point when the fluid is displaced by the steam from the test chamber (DE-OS No. 27 21 732).

With a different process (EU-OS No. 0 056 424), a sample is also taken from the liquid by means of a measuring probe and heated whereby the temperature and the temperature change in time of the heating element located in the sample is measured, and the temperature reached during a temperature change in time is registered as a measurement for the boiling point of the brake fluid.

These known processes require sample taking for each measurement, the samples being separated from the greater part of the liquid mixture and returned to it after completion of the measurement. The separation of the sample, as well as its transfer to a pressure chamber, and its heating up to a specific steam volume in the pressure chamber, which is required for each measurement, is costly and relatively complicated, and requires a relatively long time interval for heating and cooling of the sample.

OBJECT OF THE INVENTION

It is an object of the invention to provide an improved process and apparatus in which the necessary measurements can be conducted by means of a sensor which is immersible into the liquid mixture, i.e., without having to separate a sample fluid for each test process, enabling simultaneously a short sequence of checks.

SUMMARY OF THE INVENTION

The invention is based on the established fact that when heating an electric resistance wire located in the liquid mixture, which has a positive temperature coefficient, an almost sudden change in resistance occurs, whereby the evaporation temperature of the liquid mixture is exceeded, with the consequence that (a) when supplying a given and defined electric energy quantity, a spontaneous change in time interval for the energy conversion can be measured, or (b) with a given and defined time interval, a spontaneous change of the converted energy quantity is noticeable.

As the boiling point temperature of the liquid mixture changes as a function of the portion of the liquid having a lower evaporation temperature, the resistance wire can be heated in excess of the boiling point temperature by supplying an appropriate given energy quantity to the wire.

Starting out on the basis of these facts, it is, according to the invention, merely necessary, when a percentage limiting value of the portion of the liquid having a lower evaporation temperature is given, to determine the region of energy quantities supplied to the resistance wire located in the representative sample of the liquid mixture, within which the time intervals for the energy conversion change noticeably, and then to supply the energy quantities used in the sample to the resistance wire located in the liquid mixture, whereby the time intervals for the energy conversion change noticeably, and to compare the time intervals for the energy conversion with those of the sample. As long as the given percentage limiting value of the portion of the fluid having a lower evaporation temperature is not reached, energy conversion times are measured in the liquid mixture which deviate noticeably from the corresponding intervals measured in the representative sample. As soon as the given percentage limiting value of the portion of the fluid having a lower evaporation temperature is reached or exceeded, an energy conversion time is obtained which corresponds to that in the sample.

Instead of using the time intervals for the energy conversion as a measured quantity in connection with the given and defined energy quantities, the process may be reversed, whereby the time interval for supplying the electric energy is given, and the supplied energy is measured as the measured quantity, while also in this case the region of the sample is determined in which the energy conversion changes noticeable and rather suddenly, so as to supply subsequently, during the same time interval as is measured in the sample, the energy quantities determined therein to the resistance wire located in the liquid mixture, which lead to a noticeable and sudden energy conversion, and to compare the supplied energy quantity with that supplied to the resistance wire located in the sample. Until the given percentage limiting value of the portion of the liquid which has a lower evaporation temperature than the liquid mixture has been reached, the energy quantities to be compared with one another will vary, whereas they will be measured in about the same quantity when the aforesaid percentage limiting value of the portion of the liquid which has a lower evaporation temperature is reached or exceeded.

With the new process it is merely required to produce only once a representative sample of the liquid mixture for the given percentage limiting value of the portion of the liquid contained in a liquid mixture, so as to determine the measured quantities and data required for subsequent measurements in the test liquid mixture, and then to conduct any number of measurements in the test liquid mixture. The measurements in the liquid are conducted by directly immersing the resistance wire into the liquid mixture without noticeably affecting the temperature, composition, etc. of the mixture. For this reason a sequence of numerous short measurements can be conducted in the liquid mixture which, for instance, are required when by adding a portion of the liquid, a specific mixture ratio is to be produced and indicated immediately after it has been obtained.

In other cases, where only a gradual change in the mixture ratio takes place, for instance with hygroscopic liquids which take up water from the surrounding area, further measurements can be conducted in greater time intervals in the representative sample after the first determination of the appropriate measured quantities or data. The measurements of the representative sample can thus be conducted in the laboratory completely separate from later measurements in the liquid mixture.

It has proved to be particularly practical, if the electric energy quantities are supplied to the resistance wire by current impulses in the form of a charging or discharging current of a capacitor or store. Apart from the low cost involved in supplying the resistance wire with energy quantities when applying this method, the simple determination of the respective measured quantities offers a further advantage.

In the event that the time intervals of the energy conversion are provided as the measured quantity in accordance with the process, is it recommended that when supplying electric energy quantities by capacitor discharges, to measure the time intervals between the approximate maximum voltage and approximately 20% thereof as a measured quantity at the resistance wire. This process, whereby capacitor discharges and the time measurements are used, has proved itself in practical application and is distinguished by the fact that it requires very little expenditure and leads to significant and excellent reproducible results.

Particularly, when conducting measurements with larger time intervals, errors may occur caused by deviations of the supplied energy quantities, e.g., by changes in capacitance or voltage of the energy source. In order to remedy this problem, a practical development of the process provides that, in order to compensate for deviations of the supplied energy quantities, which are caused by changes in the energy source, such as capacitance changes or voltage fluctuations, the energy quantities which are provided each time for measurements to be conducted in the liquid mixture are supplied through a stabilized resistor, and the measured quantity relevant for checking the liquid mixture is determined as the actual quantity and compared with the measured quantity determined with the nominal quantity of the supplied energy quantity, and that the measured quantity determined while measuring the liquid mixture is corrected in proportion of the true value to the nominal value of the measured quantity when applying the stabilized resistor.

An exact measurement further requires that the measured quantity deviations, which are conditional upon the temperature changes in the liquid mixture, are also taken into consideration. This is particularly significant for liquid mixtures that are subject to large temperature fluctuations, such as hydraulic liquids and such. For the above reason, a further development of the process provides that in order to take the temperature changes of the test mixture into account, a resistance wire, which has the same electrical and mechanical data as the wire which is immersible into the mixture, is placed into the reference liquid which does not have the noticable measured quantity changes of the mixture, that the resistance wire located in the reference liquid is supplied with energy quantities, which each time are provided for conducting measurements in the liquid mixture, by means of current impulses at the respective operating temperature of the liquid mixture, and the measured quantities provided for measuring the liquid mixture are determined, and that in relationship to these values the true value of the measures quantity determined in the liquid mixture is corrected.

A device suitable for working the process described as the first variant, whereby the time intervals for converting the electric energy, which is supplied to the electric resistance wire, is provided as the measured quantity, is, according to the invention, characterized by the fact that a capacitor is provided as the energy source, and a resistance wire, which is immersible into the liquid mixture, is arranged in a discharge circuit of the capacitor, that the discharge circuit is equipped with an electronic measuring device and indicator measuring discharging times at the wire at the maximum voltage or approximately 20% thereof, and with a device comparing the discharging times with the nominal value, and indicating the difference thereof.

When using an electric capacitor as an energy source, a particularly simple assembly of the device results, whereby the energy quantities supplied to the resistsance wire can very easily be adjusted by changing the charging voltage of the capacitor. Devices of this type, which require a relatively low expenditure in electronic measuring devices and indicators, have already proved themselves in practical tests.

When working the process according to another variant of the invention, it is paractical to provide an electric capacitor or store as an energy source, and to arrange a resistance wire, which is immersible into a liquid mixture, in a charge circuit of the capacitor or store, while the charge circuit is equipped with an electronic measuring device and indicator which measure the energy quantity supplied to te capacitor or store during a predetermined time interval, as well as with a device which compares the the energy quantity with the nominal value and indicates the difference thereof.

Instead of using an electronic capacitor or store as an energy source, a different embodiment of device enables the use of an electric battery, which can be substituted in any of the aforementioned processes.

Irrespective of whether the aforesaid devices indicate the energy quantities or the time intervals as measured quantities, they can be developed, or further developed, so as to allow for fluctuations in the supplied energy quantities or for temperature fluctuations.

BRIEF DESCRIPTION OF THE DRAWING

The above and other objects, features and advantages of the invention will become more readily apparent from the following description, reference being made to the accompanying drawing, in which.

SPECIFIC DESCRIPTION

Figure 1:
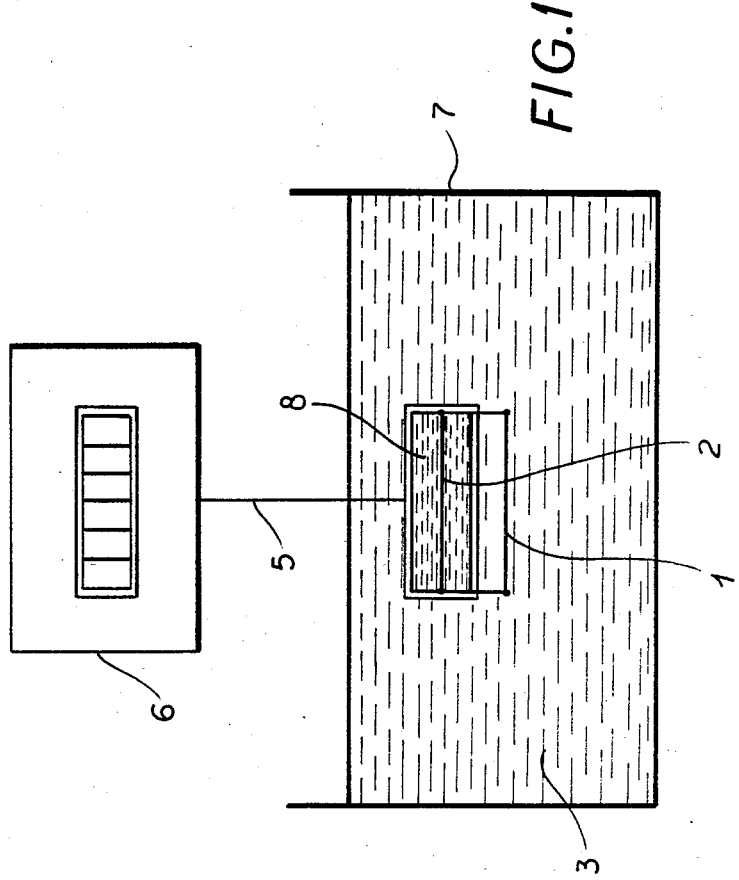
FIG. 1 is a diagrammatic view of an apparatus for carrying out the process according to the invention.

According to FIG. 1, the liquid mixture 3 to be tested is contained in a container 7 illustrated as a schematic drawing. A tightly stretched resistance wire 1, having a positive temperature coefficient, as for example a tungsten wire, is immersed into the liquid mixture. This wire 1 is attached to an ampul 4 and connected via a junction cable 5 with an electronic measuring device and indicator 6. The ampul 4 is filled with a liquid 8 whose boiling point is higher than that of the liquid mixture 3. The ampul is equipped with another resistance wire 2 which, with respect to its mechanical and electrical specifications, is equal to the resistance wire 1. The resistance wire 2 is likewise connected with the electronic measuring device and indicator 6 via the junction cable 5.

The following description describes the application of the arrangement illustrated in FIG. 1:

The electronic measuring device and indicator 6 is so designed that a chargeable capacitor contained in this device can be discharged via resistance wire 1 or resistance wire 2. The indicator displays the time interval required for discharging the capacitor, which lies between the maximum voltage value and approximately 20% thereof. It compares this discharge time with a given nominal value. At the same time, the nominal value is determined as follows with the charging and measuring device described herein: The measuring device, which is equipped with resistance wire 1 and resistance wire 2, is immersed into a representative sample of the liquid mixture where the given percentage limiting value of the portion of the liquid contained in this mixture has a lower evaporation temperature. The resistance wire 1 is heated temporarily within m sec, or a maximum of several seconds, by applying varying quantities of energy by means of electric capacitor discharges, and the discharge times are measured beteen the approximate maximum voltage and approximately 20% thereof, and the region of the energy quantities is determined within which the discharge times change noticeably. This discharge time is then entered into the electronic measuring device as the nominal value, and serves as a reference quantity for subsequent measurements in the liquid mixture. If the nominal values of the discharge times entered into the electronic measuring device are reached during a subsequent immersion of the measuring device into the liquid mixture in the course of capacitor discharges via the resistance wire 1, this will serve as a criterion that the given percentage limiting value of the portions of the liquid, which has a lower evaporation temperature, has been reached and exceeded. As the ampul 4, together with the measuring device, is immersed into the liquid, the liquid contained in the ampul and the resistance wire 2 streched therein adopt the temperature of the surrounding liquid. By discharging the capacitor via the resistance wire 2, the influence of the temperature of the liquid mixture on the discharge times can thus be determined and taken into consideration in the electronic measuring device when capacitor discharges are conducted via the resistance wire 1.

A stabilized resistor, not shown in the drawing, connectable with the capacitor can also be so arranged in the electronic measuring device 6 so that the capacitor can be discharged by means of a selector switch via this stabilized resistor. Also during this discharge operation, the discharge times are measured, so that changes in capacitance or charging voltages of the capacitor can be detected and taken into consideration when discharging the capacitor via the resistance wire 1.

The measuring device is very small in size, so that it can also be installed in brake fluid reservoirs, to be used, in connection with the electronic measuring device, as an indicator indicating when given percentage limiting values of the water taken up by the brake liquid are exceeded.

Figure 2:
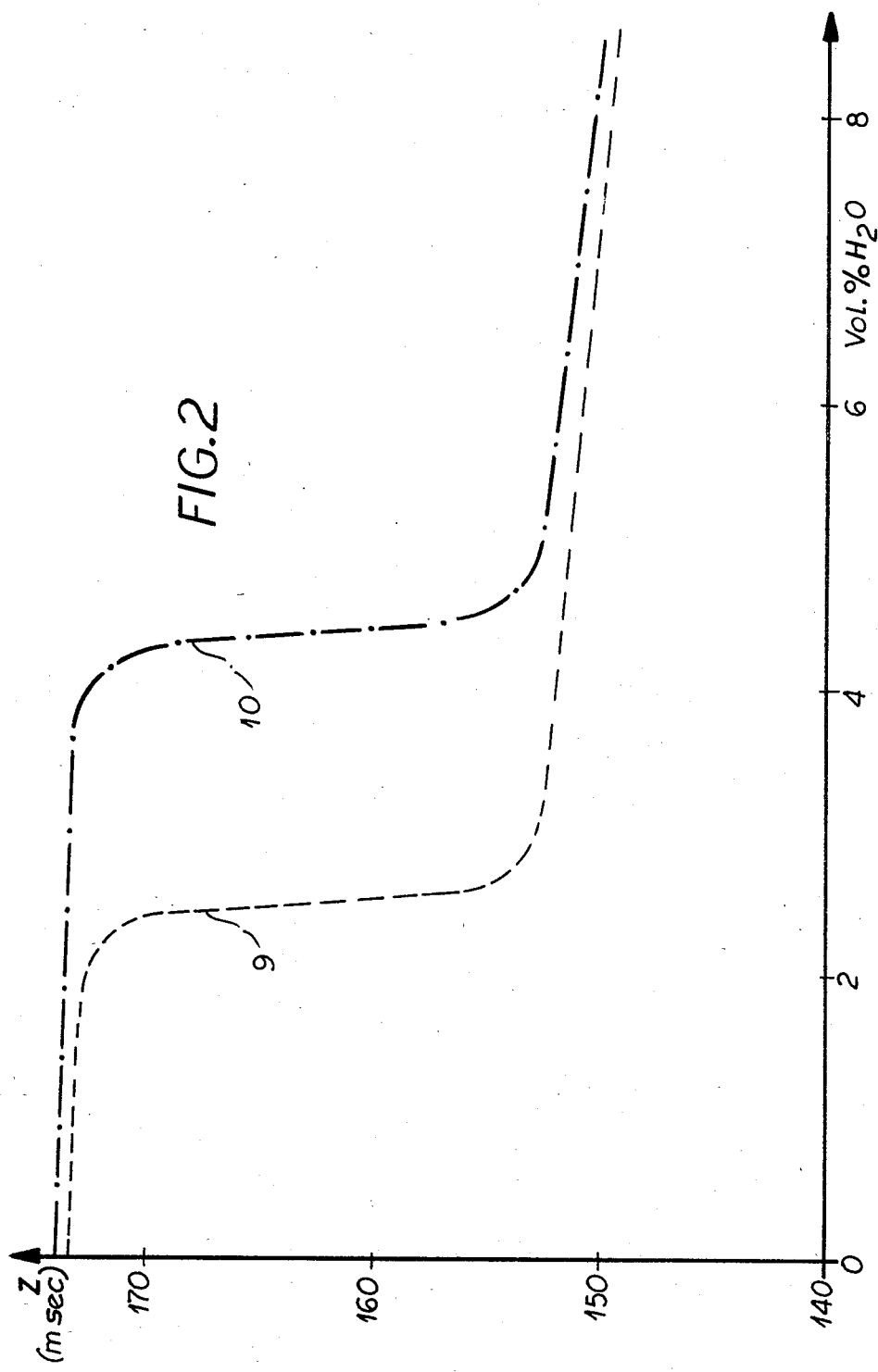
FIG. 2 is a graph showing a test result determined by the process.

In the graphical presentation according to FIG. 2, the discharge times of an electric capacitor according to FIG. 1, as a function of the water content of the two hydraulic liquids, are illustrated by curves 9 and 10. This shows that in curve 9 a sudden change of the discharge times occurs in the liquid measuring between 2.2 and 2.3 vol. % water, whereas in curve 10 this change measures between 4.1 and 4.2 vol. % water.

The curves indicate a significant change in the discharge times which in certain regions occurs only with negligible changes of the water content in the hydraulic liquid.

For each percent of water content in the hydraulic liquid, curves similar to those illustrated in FIG. 2 can be constructed if the electric resistance wire is supplied with suitable energy quantities.

Similar curves, as illustrated in FIG. 2, also result if other measured quantities are determined in connection with this process.

Figure 3:
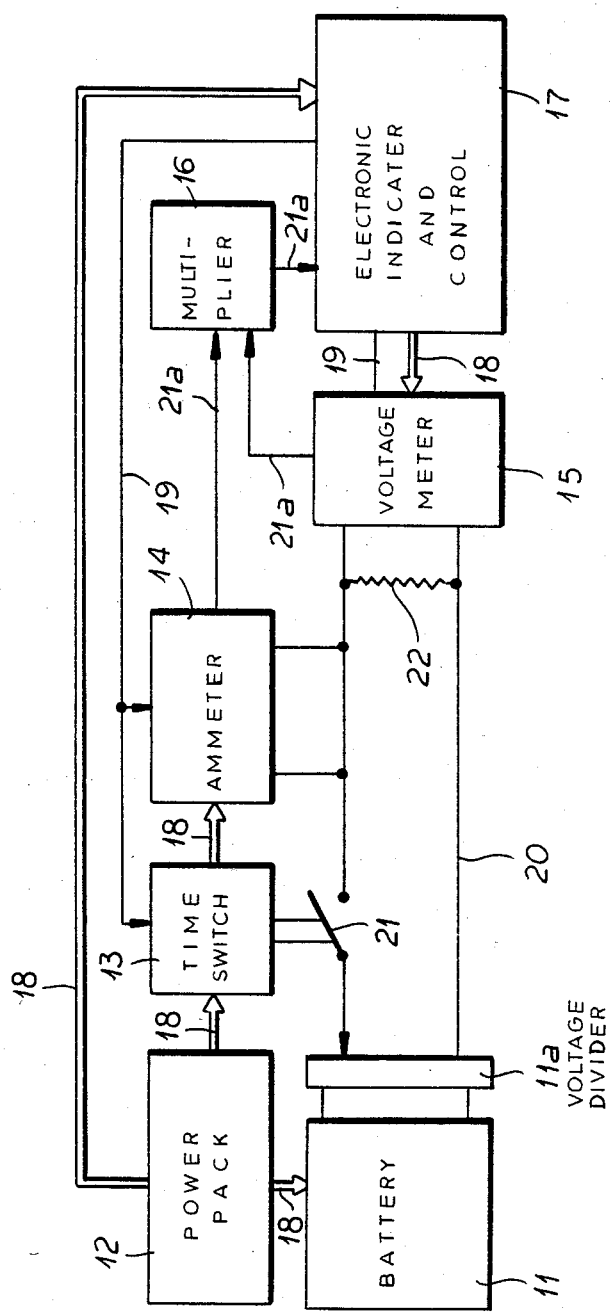
FIG. 3 is a block diagram showing the circuit of the device using a battery as an energy source.

The block diagram illustrated in FIG. 3 shows an arrangement using a battery 11 in connection with a voltage divider 11a as an energy source. A power pack 12 is connected to the battery, which takes over the recharging of the battery 11, as well as the power supply of an adjustable time switch 13, an integrating ammeter 14 and integrating voltage meter 15, and of the electronic indicater and control 17 via utility lines designated as 18. The elements 13, 14, 15, as well as 16 and 17 are also connected via control lines.

The voltage divider 11a is connected with the electric resistance wire 22, which is immersable into the liquid mixture, via supply lines 20 in which the switch 21 is arranged. The integrating ammeter 14 is also arranged in the supply line 20, which, like the integrating voltage meter 15, is connected with the multiplier 16 via signalling line 21a, which is connected with the electronic indicator and control 17 via a further signalling line 21a.

By means of the time switch 13 or switch 21, varying energy quantities can be supplied to the electric resistance wire 22 from the battery 11 via the voltage divider 11a, the conversion of which is indicated each time in the electronic indicator and control 17. Due to changes in the energy quantities supplied to the resistance wire 22, the region, in which the sudden change of energy conversion occurs, can be determined.

The resistance wire 22 corresponds to the resistance wire 1 shown in FIG. 1, and can also be arranged parallel to a further resistance wire 2 located in an ampul 4, as is illustrated in FIG. 1.

The immersible test sensor, which is illustrated schematically in FIG. 1, may be very small in size, so as to be able to be installed in brake fluid reservoirs of motor vehicle, so that, in connection with the electronic measuring device, it can be used as an indicater indicating when given percentage limiting values of the water taken up by the brake liquid are exceeded.

Since, due to the relatively short application of electric energy to the electric resistance wire, a vapor zone surrounding the wire will occur only during a very short interval, which is absorbed by the surrounding liquid, vapor bubbles will not occur, so that repeated measurements are by all means possible, and that measurements can also be conducted in highly flammable or combustible liquid mixtures.

We claim:

1. A process for determining the percentage of a given liquid in a liquid mixture, said given liquid having a lower evaporation temperature than said mixture, comprising the steps of:
   (a) immersing an electric resistance wire having a positive temperature coefficient in a sample of a known composition of said mixture;
   (b) temporarily rapidly heating said resistance wire by applying varying quantities of energy thereto in the form of electric current impulses;
   (c) measuring as a measured quantity the time intervals required for energy conversion to occur in said resistance wire and determining the region of the energy quantities within which the time intervals of the energy conversions change noticeably and suddenly; and
   (d) immersing said resistance wire into a test sample of a liquid mixture of unknown composition and applying to the resistance wire in said test sample the quantities of energy determined with said sample of known composition, whereby when the measured time intervals change noticeably, said intervals are compared with the intervals determined with said sample of known composition to establish the percentage of said given liquid in said test sample.

2. The process defined in claim 1 wherein said resistance wire is supplied with electric energy quantities or current impulses in the form of a charging or discharging current from a capacitor or battery.

3. The process defined in claim 2 wherein when supplying electric energy quantities to said resistance wire by capacitor discharge, the time intervals measured are between approximate maximum voltage and 20% thereof.

4. The process defined in claim 1 wherein deviations of the supplied energy quantities caused by changes in the output of the energy source are compensated for by feeding the energy quantities through a stablizing resistor and determining the compensated energy quantities produced thereby, said compensated energy quantities being compared with those determined in step (c) and corrected in relationship thereto.

5. The process defined in claim 1 comprising the further steps of:
   immersing a second resistance wire having electrical and mechanical characteristics identical to those of said first mentioned resistance wire into a reference liquid mixture at the same temperature as said liquid mixture and free of said given liquid;
   applying varying quantities of energy to said second resistance wire as in step (b);
   determining the region of energy conversion as in step (c); and
   immersing said first resistance wire into a test sample of said liquid mixture of unknown composition as in step (d) and comparing the values derived therefrom with the values derived using said reference liquid mixture, whereby the effects of temperature changes on said liquid mixture of unknown composition can be compensated for.

6. A process for determining the percentage of a given liquid in a liquid mixture, said given liquid having a lower evaporation temperature than said mixture, comprising the steps of:
   (a) immersing an electric resistance wire having a positive temperature coefficient in a sample of a known composition of said liquid mixture;
   (b) heating said resistance wire by applying electric current impulses thereto for a constant and specific time intervale ranging between 1 millisecond to several seconds;
   (c) measuring as a measured quantity the energy quantity applied to said resistance wire and determining the region within which the energy conversions change noticeably and suddenly by changing the energy quantity applied to said resistance wire; and
   (d) immersing said resistance wire into a test sample of a liquid mixture of unknown composition and applying to said resistance wire in said sample the same energy quantities for the same time intervals as with said sample of known composition, whereby when the energy conversion changes noticeably, the applied energy quantity is compared with the quantities determined with said sample of known composition to establish the percentage of said given liquid in said test sample.

7. An apparatus for determining the percentage of a given liquid in a liquid mixture, said given liquid having a lower evaporation temperature than said mixture, said apparatus comprising:
   an energy source formed by a capacitor arranged in a discharge circuit;
   an electric resistance wire having a positive temperature coefficient arranged in said circuit and adapted to be immersible in a test sample of a liquid mixture of unknown composition;
   switch means in said circuit for opening and closing same; and
   an electronic measuring device arranged in said circuit and provided with an indicator for displaying the discharge times, when said switch means is closed, of said capacitor at said resistance wire between the maximum voltage and approximately 20% thereof, said device comparing the discharge times with a nominal value and displaying the differences therewith on said indicator to establish the percentage of said given liquid in said test sample.

8. The apparatus defined in claim 7, further comprising a stabilizing resistor connectable in parallel with said resistance wire by a selector provided in said discharge circuit.

9. The apparatus defined in claim 7, further comprising a second resistance wire having electrical and mechanical characteristics identical to those of said first mentioned resistance wire, said second resistance wire being connectable in parallel with said first resistance wire by a selector provided in said discharge circuit, said second resistance wire being sealed in an ampul filled with a reference liquid mixture free of said given liquid and adapted to be immersible in said test sample of a liquid mixture of unknown composition, whereby said reference liquid mixture in said ampul is brought into temperature equilibrium with said test sample enabling the establishment of said nominal values when said first resistance wire is disconnected from said discharge circuit by said selector and current is passed through said second resistance wire.

10. An apparatus for determining the percentage of a given liquid in a liquid mixture, said given liquid having a lower evaporation temperature than said mixture, said apparatus comprising:
   an energy source arranged in a discharge circuit;
   an electric resistance wire having a positive temperature coefficient arranged in said circuit and adapted to be immersible in a test sample of a liquid mixture of unknown composition;

switch means in said circuit for opening and closing same; and an electronic measuring device arranged in said circuit and provided with an indicator for displaying the energy quantity supplied, when said switch means is closed, to said resistance wire within a predetermined time interval, said device comparing the energy quantity with a nominal value and displaying the difference therewith on said indicator to establish the percentage of said given liquid in said test sample.

11. The apparatus defined in claim 10 wherein said energy source is a capacitor.

12. The apparatus defined in claim 10 wherein said energy source is a battery.

* * * * *